(12) United States Patent
Matthiassen

(10) Patent No.: US 10,112,031 B2
(45) Date of Patent: Oct. 30, 2018

(54) CATHETER PACKAGED INSIDE OF A HANDLE ATTACHED TO A CONTAINER

(71) Applicant: Coloplast A/S, Humlebaek (DK)

(72) Inventor: Benny Matthiassen, Lyngby (DK)

(73) Assignee: Coloplast A/S, Humlebaek (DK)

( * ) Notice: Subject to any disclaimer, the term of this patent is extended or adjusted under 35 U.S.C. 154(b) by 289 days.

(21) Appl. No.: 14/915,908

(22) PCT Filed: Sep. 1, 2014

(86) PCT No.: PCT/EP2014/068490
§ 371 (c)(1),
(2) Date: Mar. 2, 2016

(87) PCT Pub. No.: WO2015/028658
PCT Pub. Date: Mar. 5, 2015

(65) Prior Publication Data
US 2016/0193447 A1    Jul. 7, 2016

(30) Foreign Application Priority Data

Sep. 2, 2013 (DK) .................... 2013 70487

(51) Int. Cl.
*A61M 25/01* (2006.01)
*A61M 39/22* (2006.01)
*A61M 25/00* (2006.01)

(52) U.S. Cl.
CPC ...... *A61M 25/0136* (2013.01); *A61M 25/002* (2013.01); *A61M 25/0017* (2013.01); *A61M 39/22* (2013.01); *A61M 2025/0175* (2013.01)

(58) Field of Classification Search
CPC .. A61M 2025/0175; A61M 2039/1027; A61M 2039/24; A61M 2039/267; A61M 2039/268; A61M 25/0017; A61M 25/002; A61M 25/0136; A61M 39/22; A61M 39/26; B65D 47/243; B65D 47/247; B65D 47/248; B65D 47/26; B65D 47/263;
(Continued)

(56) References Cited

U.S. PATENT DOCUMENTS 3,838,843 A * 10/1974 Bernhard ........... A61B 5/15003
                                                       251/149.1
3,985,332 A * 10/1976 Walker ................... F16K 1/302
                                                       222/147
4,055,179 A   10/1977 Manschot et al.
(Continued)

FOREIGN PATENT DOCUMENTS

RU    2434654 C2    11/2011
SU    1528505 A1    12/1989
(Continued)

*Primary Examiner* — Adam Marcetich
(74) *Attorney, Agent, or Firm* — Coloplast Corp., Coloplast A/S; Nick Baumann

(57) ABSTRACT

A catheter assembly includes a catheter packaged inside of a handle that is attached to a container. The catheter has a distal end portion that includes a valve. The valve includes a protrusion coupled to an exterior of a distal end portion of the catheter. The handle has a cavity with a flange is formed on an interior surface of the cavity. The flange is sized to engage with the protrusion coupled to the catheter, and the valve of the catheter opens when the protrusion of the catheter contacts the flange.

13 Claims, 3 Drawing Sheets

(58) Field of Classification Search
CPC ....... B65D 47/28; B65D 47/283; F16K 3/265; F16K 3/267
See application file for complete search history.

(56) References Cited

U.S. PATENT DOCUMENTS

| | | | | |
|---|---|---|---|---|
| 4,066,080 | A * | 1/1978 | Sneider | A61M 3/0262 222/105 |
| 4,200,097 | A * | 4/1980 | Hobbs, Jr. | A61M 3/0262 604/213 |
| 4,324,242 | A * | 4/1982 | Cross | A61M 3/0262 604/213 |
| 4,519,794 | A * | 5/1985 | Sneider | A61M 3/0262 222/544 |
| 4,846,816 | A | 7/1989 | Manfredi | |
| 5,156,603 | A | 10/1992 | Olsen | |
| 6,119,719 | A * | 9/2000 | Viegener | F16K 5/0414 137/454.5 |
| 6,543,745 | B1 * | 4/2003 | Enerson | A61M 39/26 251/149.7 |
| 6,902,146 | B1 * | 6/2005 | Elliott | A61F 5/4405 251/351 |
| 2002/0017538 | A1 * | 2/2002 | Vakiener | B65D 47/06 222/525 |
| 2003/0004496 | A1 | 1/2003 | Tanghoj | |
| 2003/0060807 | A1 | 3/2003 | Tanghoj et al. | |
| 2004/0158231 | A1 | 8/2004 | Tanghoj et al. | |
| 2005/0124946 | A1 * | 6/2005 | Landau | A61M 3/0262 604/317 |
| 2009/0229671 | A1 * | 9/2009 | Hartnett | A61M 39/22 137/13 |
| 2010/0007134 | A1 * | 1/2010 | Elton | A61M 39/10 285/31 |
| 2011/0106046 | A1 * | 5/2011 | Hiranuma | A61J 1/2096 604/414 |
| 2011/0106060 | A1 * | 5/2011 | Atkinson | A61M 25/0017 604/544 |
| 2011/0108613 | A1 * | 5/2011 | Stribling | A47G 21/185 229/103.1 |
| 2012/0110951 | A1 * | 5/2012 | van Groningen | A61M 25/002 53/425 |
| 2012/0325692 | A1 | 12/2012 | Tanghoj et al. | |
| 2013/0167960 | A1 * | 7/2013 | Pethe | F17C 13/00 137/798 |
| 2013/0197485 | A1 * | 8/2013 | Gardner | A61M 39/162 604/533 |
| 2013/0338616 | A1 * | 12/2013 | Galindo | A61F 5/4405 604/335 |
| 2014/0023297 | A1 * | 1/2014 | Zund | B65D 47/248 383/43 |
| 2015/0173937 | A1 * | 6/2015 | Jackson | A61F 5/4405 604/318 |
| 2016/0038717 | A1 * | 2/2016 | Murray | A61M 25/0017 604/544 |

FOREIGN PATENT DOCUMENTS

| | | |
|---|---|---|
| WO | 2004089454 A1 | 10/2004 |
| WO | 2008009590 A1 | 1/2008 |
| WO | 2012060699 A1 | 5/2012 |
| WO | 2013029620 A1 | 3/2013 |
| WO | 2013029621 A1 | 3/2013 |
| WO | 13057517 | 4/2013 |
| WO | 2013075725 A1 | 5/2013 |

* cited by examiner

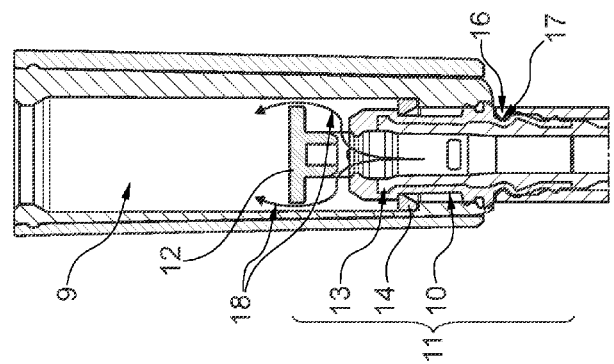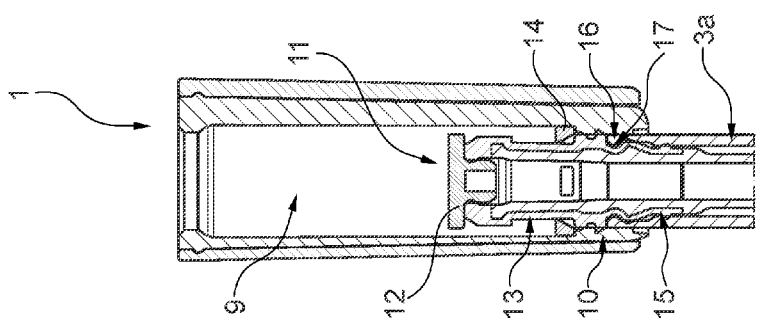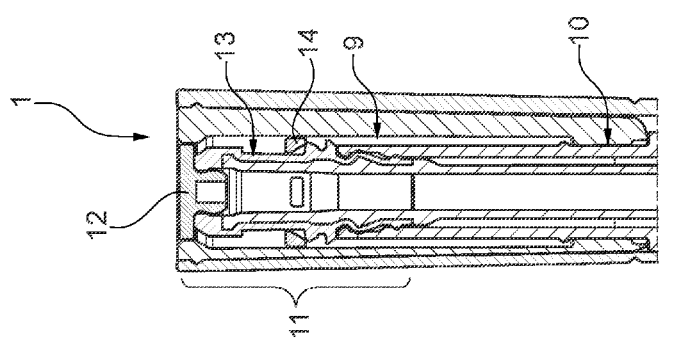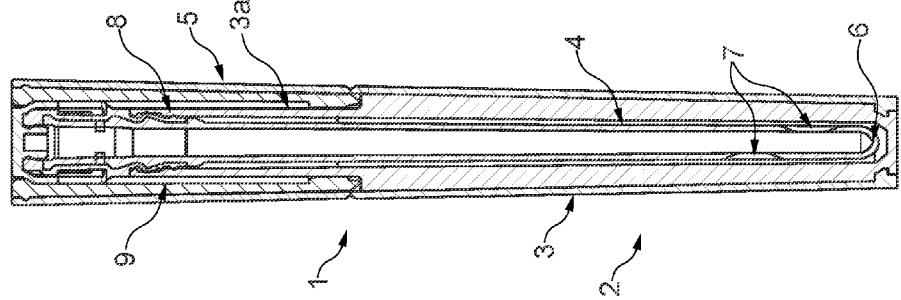

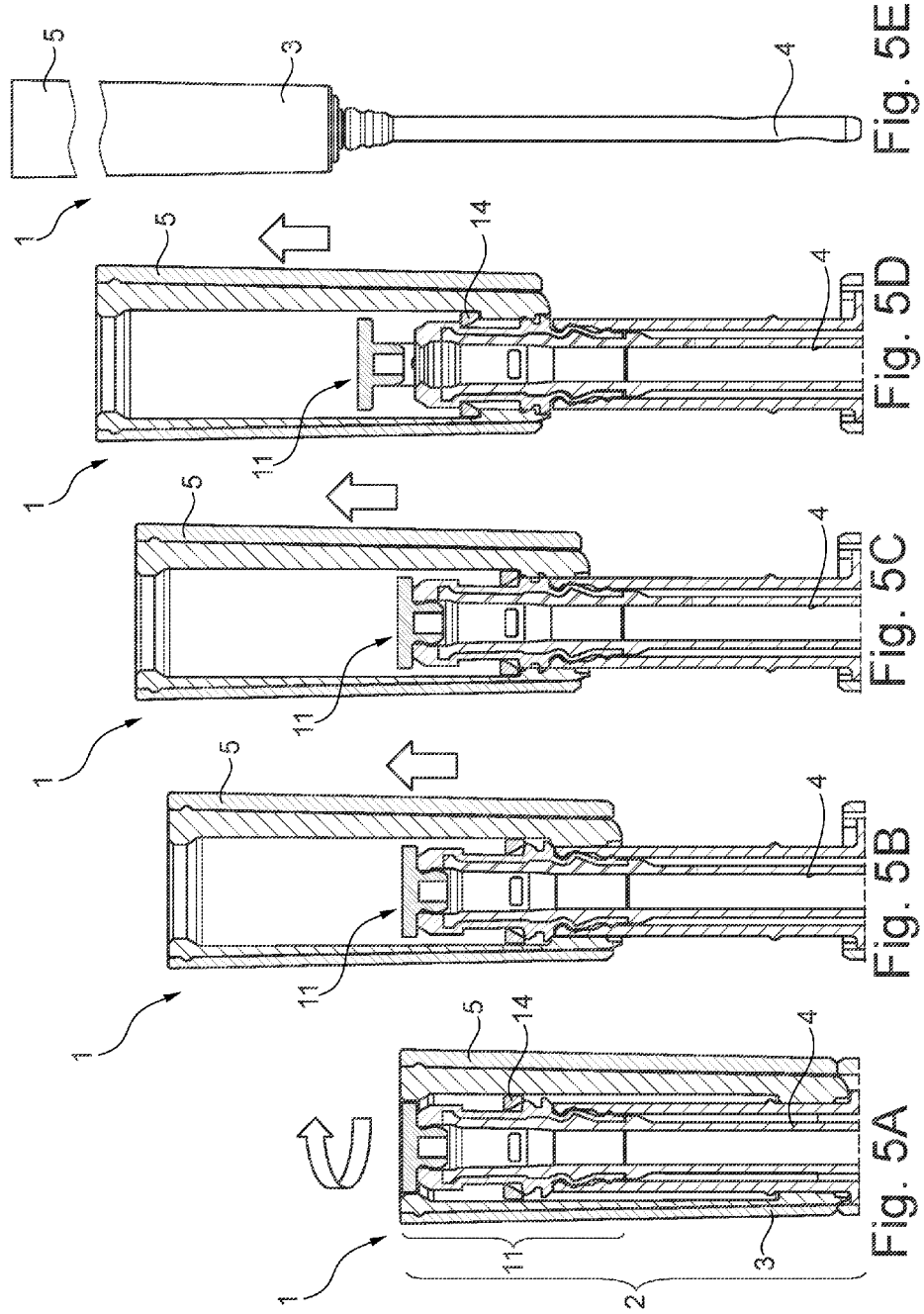

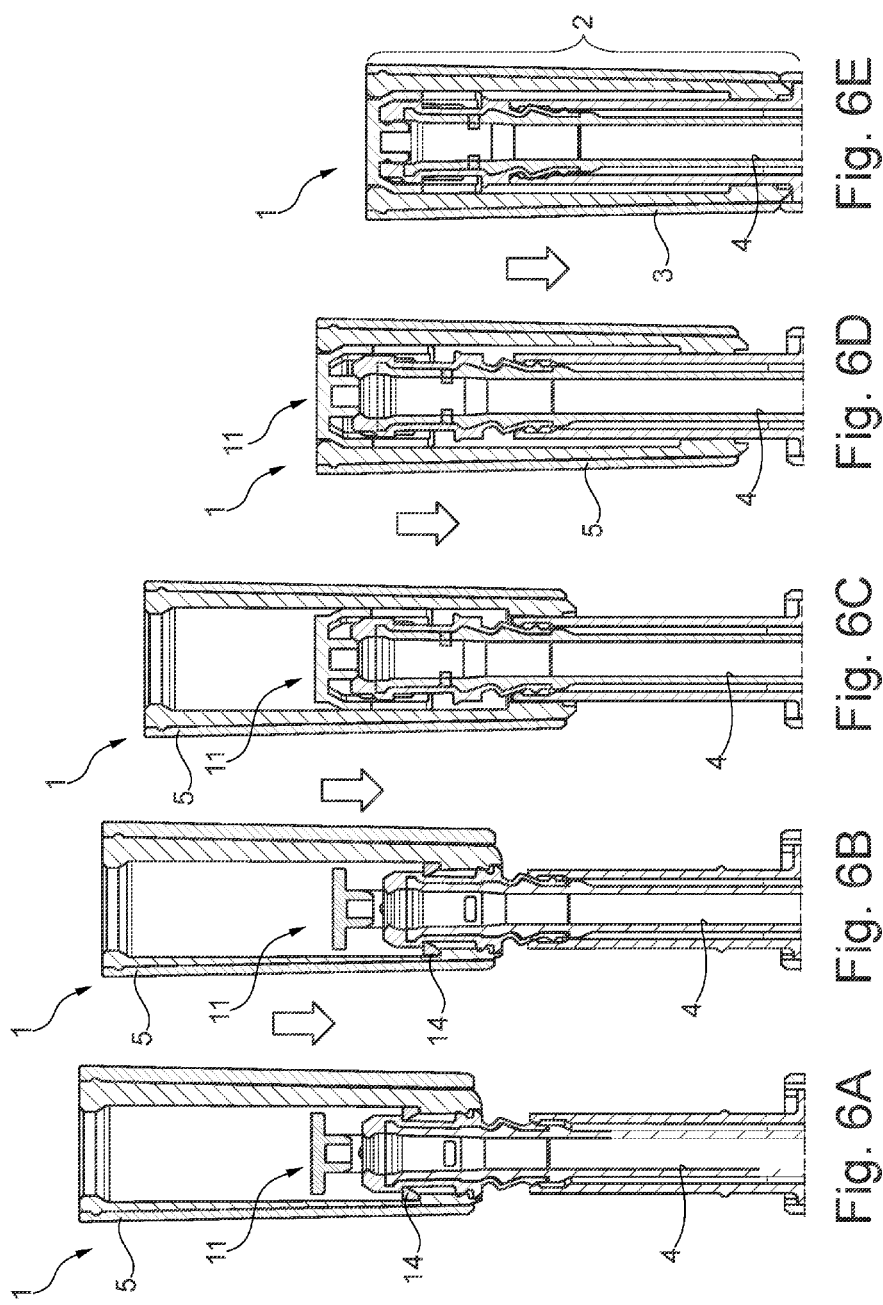

CATHETER PACKAGED INSIDE OF A HANDLE ATTACHED TO A CONTAINER

The invention relates to a catheter assembly and more particular to an assembly that can be stored in a compact configuration.

BACKGROUND

Urinary catheter assemblies for draining the bladder are increasingly used for intermittent as well as indwelling or permanent catheterisation. Typically, urinary catheters are used by patients suffering from urinary incontinence or by disabled individuals like paraplegics or tetraplegics, who may have no control permitting voluntary urination and for whom catheterisation may be the way of urinating.

Urinary catheters are divided into two major groups of catheters, indwelling catheters and intermittent catheters. Indwelling catheters are typically inserted into the urethra and the bladder by medical personal (i.e. a trained professional, typically a nurse or physician) and has means for retaining the catheter inside the bladder for up to two weeks or more. Indwelling catheters are soft and flexible since they have to remain in the urethra for weeks. Indwelling catheters empty the bladder continuously.

Intermittent catheters are typically inserted by the user him- or herself and sits only in the urethra and bladder for as long as it take to empty the bladder—e.g. for about 5-10 minutes. Intermittent catheters are used every 4-6 hours to empty the bladder corresponding roughly to the interval that people having no urinary problems will usually go to the bathroom. Intermittent catheters are typically more rigid than indwelling catheters since they have to be inserted by the user him-/herself and since they do not need to sit in the urethra for days or weeks. An important feature for the intermittent catheter is to ease the insertion into the urethra. This is done by providing the intermittent catheter with a low frictious surface. Non-limiting examples of such are hydrophilic coated catheters which are subsequently wetted by a swelling media in order to produce a low friction surface, or oil or water based gel which is applied to the catheter before insertion into the urethra.

Intermittent urinary catheters may be provided with a hydrophilic coating that needs to be wetted prior to use and thereby absorbs a considerable amount of liquid. Such a hydrophilic coating will provide a very lubricious surface that has very low-friction when the catheter is to be inserted. Hydrophilic coated catheters, where the coating absorbs a considerable amount of liquid for a low frictious surface (swelling degree>100%), will not be suitable for indwelling catheters, because the hydrophilic surface coating would stick inside the mucosa of the urethra if left inside the body for a longer period, due to the hydrophilic coating transforming from being highly lubricious when fully wetted to being adhesive when the hydration level of the coating is reduced.

This invention relates to intermittent catheters with a hydrophilic coating of the kind that is wetted prior to use to absorb a considerable amount of liquid and to provide a very lubricious surface.

Description of Related Art

WO2013029620 discloses a catheter kit comprising a catheter and a urine bag stored in a package wherein flow is prevented between the catheter and urine bag when stored but enabled when the kit is used.

SUMMARY OF THE INVENTION

The invention relates to a catheter assembly with a handle telescopically connected to the catheter. This allows the catheter assembly to assume at least three well-defined configurations, a storage configuration, a coupling configuration and a use-configuration. In the storage configuration, the assembly is compact and the handle receives the distal end of the catheter inside it. In the coupling configuration, the handle is extended to make room for connecting a collecting bag or tube to the handle, but the catheter is still stored inside the package in a sealed condition. In the use configuration, the package can be removed from the catheter and the catheter is ready-to-use. This assembly allows the user to prepare the assembly completely, including connecting a collecting bag or tube to the assembly, and still keep the catheter sterilely stored. Only when the user is ready, the sterile seal to the catheter is broken and the catheter can be removed from the package and used.

BRIEF DESCRIPTION OF THE DRAWINGS

FIG. 1 illustrates a catheter assembly according to the invention.

FIG. 2 illustrates a close-up of the handle in a storage configuration.

FIG. 3 illustrates a close-up of the handle in a coupling configuration.

FIG. 4 illustrates a close-up of the handle in a use-configuration.

FIGS. 5A-5D illustrate the catheter assembly of FIG. 1 in a sequence of opening steps with FIG. 5E showing the catheter assembly opened.

FIGS. 6A-6D illustrate the catheter assembly in a sequence of re-closing steps, with FIG. 6E showing catheter assembly as a package.

DETAILED DESCRIPTION OF THE INVENTION

The invention relates to a catheter assembly having at least three configurations, a storage configuration, a coupling configuration and a use-configuration, the assembly comprising a package and a catheter, the package having a container defining a first cavity for receiving the catheter in the storage configuration and in the coupling configuration, the catheter having a handle detachably attached to the container, the handle being telescopically connected to the catheter, the handle being provided with a second cavity, so that the handle in the storage configuration is configured to receive a distal end of the catheter, the handle being configured to receive a connector to a bag or tube in the coupling configuration and in the use configuration, the catheter being provided with a valve in the distal end, the valve being configured to cooperate with means functioning as a stop in the handle so that the valve remains closed in the storage configuration and in the coupling configuration, and opens, when the catheter assembly is brought from the coupling configuration to the use-configuration.

An assembly as described above provides the opportunity for attaching a tube or collecting bag to the catheter assembly, while the sterility of the catheter is still maintained. The second cavity includes the distal part of the catheter during storage and can be used for attaching a urine bag during use.

The connection of the collecting bag or the tube to the catheter assembly is easier with an assembly as claimed, because the user does not need to worry about where to put the catheter as the collecting bag or tube is connected. The catheter is still sterilely stored inside the container and the container can be put on a table or in the user's lap during connection without any risk of infecting the catheter or spilling the swelling medium on the user's clothes.

In the following, whenever referring to a proximal end of an element of the invention, the referral is to the end adapted for insertion. Whenever referring to the distal end of an element, the referral is to the end opposite the insertion end. In other words, the proximal end is the end closest to the user, when the catheter is to be inserted and the distal end is the opposite end—the end furthest away from the user when the catheter is to be inserted. The same definitions apply to the package and container—the proximal end is the end storing the proximal end of the catheter and the distal end is the opposite end.

The catheter described in this application may be used as a urinary catheter.

The catheter comprises a main tubular part extending from the distal end to the proximal end. The tip is positioned in the proximal end of the catheter and is provided as a rounded closed end of the tube constituting the main part of the catheter. Usually catheters used for urinary drainage are from size 8 FR to size 18 FR. FR (or French size or Charriere (Ch)) is a standard gauge for catheters approximately corresponding to the outer circumference in mm. More accurately, the outer diameter of the catheter in mm corresponds to FR divided by 3. Thus, 8 FR corresponds to a catheter with an outer diameter of 2.7 mm and 18 FR corresponds to a catheter with an outer diameter of 6 mm.

Catheters of this invention may prior to use be provided with a hydrophilic coating so as to impart a low-friction insertion.

In one embodiment, the catheter is a telescopic catheter meaning that the catheter itself comprises an inner catheter part and an outer catheter part connected by a coupling, so that the inner part can be telescopically extended with respect to the outer part. The catheter may thus correspond to SpeediCath Compact Male® marketed by Coloplast A/S.

The first cavity of the catheter package may comprise a medium for activating the hydrophilic surface coating of the catheter. The activating medium may be a water based substance, such as sterile water, saline-solution, or any water based liquid. Furthermore, the activating medium may be in the form of a vapour contributing material, such as a wetted sponge, woven or non-woven material comprising a vapour contributing liquid. By introducing a vapour contributing material into the package, the vapour will over time hydrate the hydrophilic coating ensuring that the coating is activated and that the hydrophilic coating provides a low-friction surface for the catheter.

In an embodiment, an insertable part of the catheter is provided with a hydrophilic coating. In this embodiment, the cavity of the container may be adapted to receive the insertable part of the catheter.

In an embodiment, the valve is provided with valve opening means that cooperates with the means functioning as a stop in the proximal end of the handle. The cooperation between the valve opening means and the stop ensures that the valve is only opened when the catheter is extended to the stop.

The means functioning as a stop may be provided as an inwardly extending flange at the proximal end of the valve.

The valve opening means may be provided as a protrusion extending in the radial direction positioned proximally of the valve seat.

In an embodiment, the catheter is provided with a seal surrounding the distal end of the catheter so as to prevent urine from flowing out between the handle and the catheter at the distal end of the catheter.

In an embodiment, the handle is provided with a seal at the distal end. The seal assists in keeping the valve closed during sterilization where the pressure inside the package may increase.

In an embodiment, the catheter and container are provided with a snap-fit for attaching the container to the catheter. In a related embodiment, the catheter is provided with a groove at the distal end for cooperating with a ridge provided at the distal end of the container. As long as the distal end of the catheter is positioned inside the cavity of the handle—e.g. in storage configuration and coupling configuration—the ridge of the container is prevented from releasing itself from the groove at the catheter. When the catheter has been telescopically extended completely out of the cavity, the ridge will be able to release itself from the groove, because it is allowed to move slightly radially outwards with respect to the catheter. This releases the ridge from the groove and thus the container can be removed from the catheter. The cooperation between the catheter and container may of course be done by other means—e.g. the ridge may be positioned at the catheter and the groove at the container.

A snap-fit ensures that the catheter is completely extended before the container can be removed. This means that the snap-fit assists in ensuring that the valve in the catheter is opened and further that the seal between the catheter and the cavity of the handle is positioned correctly prior to use. Thus, urine drained into the catheter can escape through the valve and will be prevented from escaping between the handle and the catheter.

In an embodiment of the invention, the handle is configured to receive a male luer. Connections to bags or tubes may often comprise a male luer. By configuring the handle to directly receive a male luer, the assembly can be directly coupled to many collecting bags or tubes.

DETAILED DESCRIPTION OF THE DRAWING

Initially, it shall be noted that the figures are schematic illustrations intended only to address the principles and functions of the catheter assembly according to the invention and are not to be considered limiting to the scope of the attached claims. Furthermore, the figures and particularly the individually illustrated elements are not necessarily to scale, neither individually nor in relation to each other FIG. 1 illustrates the catheter assembly 1 in a storage configuration. The assembly comprises a package 2 with a container 3 and a catheter 4 with a handle 5. The container 3 comprises a neck portion 3a that fits tightly around a distal part of the catheter 4. In the storage configuration, the catheter assembly is compact when compared to the use configuration because the handle of the catheter is telescopically collapsed with respect to the catheter and the neck portion 3a of the container. In other words, the distal part of the catheter and the neck portion 3a are received inside the handle as illustrated in the figure. The catheter 4 has a proximal insertion end 6 provided with eyelets 7 functioning as inlets for the urine. The distal end 8 of the catheter is inside the cavity 9 of the handle 5.

FIG. 2 illustrates a close-up of the handle 5 in the storage configuration. The handle 5 is provided with an inwardly extending flange 10 functioning as a stop at the proximal end of the handle. The flange 10 cooperates with a valve 11 positioned in the distal end of the catheter. The valve 11 has a valve seat 12 providing the closure and a seal 13 so that the valve is liquid tight when it is closed—as in the position of FIG. 2. The valve is further provided with valve opening means in form of a protrusion 14 at the proximal end of the valve for cooperating with the means functioning as a stop in form of the flange 10 of the handle.

FIG. 3 illustrates a close-up of the handle 5 in the coupling configuration. The cavity 9 of the handle provides room for a connector—e.g. a male luer—on a tube or a collecting bag. The figure shows that the valve 11 is still closed; the valve seat 12 is in the closed position. Thus, the catheter is still sealed by the seal 13. Furthermore, in this position the container 3 is prevented from being removed from the catheter 2. This appears from the figure as the neck portion 3a is snap-locked to the seal on the distal end 15 the catheter 4 by a ridge 16 on the container and a groove 17 in the seal.

FIG. 4 illustrates a close-up of the handle 5 in the use configuration. The cavity 9 of the handle provides room for e.g. a male luer on a tube or a collecting bag as is easily seen in the figure. The figure shows that the valve 11 is open; the valve seat 12 is moved away from the seal 13 due to the protrusion 14 being in contact with the flange 10 of the handle. Thus, liquid (urine) can flow through the catheter and into the handle as indicated at 18. In the use configuration illustrated in FIG. 4, the container 3 can be removed from the catheter 2, because the ridge 16 is no longer within the handle 5, but is able to move slightly radially outwards and thus release the groove 17.

FIG. 5A-5D illustrate the handle 5 in a sequence of opening steps. The left-most FIG. 5A illustrates the catheter assembly in storage configuration, where the assembly is compact. The right-most FIG. 5E illustrates the catheter when it is ready to use.

FIGS. 6A-6D illustrate the handle 5 in a sequence of re-closing steps. The left-most FIG. 6A illustrates the catheter assembly in a use-condition, where the catheter is telescopically extended with respect to the handle. The right-most FIG. 6E illustrates the catheter assembly in a re-closed position that corresponds to the storage configuration. In this position the catheter assembly is completely resealed and can therefore be stored in a bag for discarding later.

The invention claimed is:

1. A catheter assembly comprising:
   a catheter packaged inside of a handle that is attached to a container;
   wherein the catheter has a proximal end portion that is insertable into a urethra and a distal end portion that includes a valve, where the valve includes a valve seat formed inside of the distal end portion of the catheter and a protrusion is located inside the handle and movable relative to the valve;
   wherein the handle has a cavity extending between a proximal end portion and a distal end portion of the handle, where the distal end portion of the handle is engaged with the valve seat of the catheter to close the valve of the catheter, and where the container is removable from the proximal end portion of the handle to disengage the distal end portion of the handle from the valve seat of the catheter and to expose the proximal end portion of the catheter; and
   wherein a flange is formed on an interior surface of the cavity of the handle, and the flange is sized to engage with the protrusion coupled to the exterior of the distal end portion of the catheter;
   wherein the valve of the catheter opens when the protrusion of the catheter contacts the flange.

2. The catheter assembly of claim 1, wherein the catheter includes a seal surrounding the exterior of the distal end portion of the catheter.

3. The catheter assembly of claim 1, wherein the catheter includes a seal surrounding the exterior of the distal end portion of the catheter.

4. The catheter assembly of claim 1, wherein an interior of the distal end portion of the handle includes a radial seal that is adapted to engage with the valve seat of the catheter.

5. The catheter assembly of claim 1, wherein the distal end portion of the catheter includes a groove that is sized to receive a ridge formed at a distal end portion of the container, and the groove and the ridge provide a snap-fit device between the container and the catheter.

6. The catheter assembly of claim 1, wherein the catheter includes a hydrophilic coating.

7. The catheter assembly of claim 1, wherein the distal end portion of the handle is attachable to one of a male luer of a urine flow tube or a urine collection bag.

8. The catheter assembly of claim 1, wherein the catheter is a telescopic catheter that is adapted to move in a proximal direction out of the handle.

9. The catheter assembly of claim 1, wherein the container is attached to the handle and the distal end portion of the handle engaged with the valve seat of the catheter to provide a closed package configured to maintain sterility of the catheter.

10. The catheter assembly of claim 1, wherein the catheter has a hydrophilic coating and the container includes water adapted to activate the hydrophilic coating on the catheter.

11. The catheter assembly of claim 1, wherein a ridge formed at a distal end portion of the container is engaged with a groove formed at the distal end portion of the catheter, and the container is adapted to transport the distal end portion of the catheter to the proximal end portion of the handle prior to disengagement of the ridge from the groove.

12. The catheter assembly of claim 1 comprising a storage configuration with a distal end portion of the container attached to the distal end portion of the catheter and the distal end portion of the catheter attached to the distal end portion of the handle.

13. The catheter assembly of claim 1 comprising a storage configuration wherein an exterior surface of the handle forms an exterior surface of the catheter assembly.

* * * * *